United States Patent [19]

Uhrig et al.

[11] Patent Number: 5,372,747
[45] Date of Patent: Dec. 13, 1994

[54] MODIFIED BLOCK POLYMERS, THEIR PREPARATION AND THEIR USE

[75] Inventors: Heinz Uhrig, Steinbach; Joachim Weide, Kelkheim, both of Germany

[73] Assignee: Hoechst Aktiengesellschaft, Frankfurt, Germany

[21] Appl. No.: 844,946

[22] Filed: Mar. 2, 1992

Related U.S. Application Data

[63] Continuation of Ser. No. 638,024, Jan. 7, 1991, abandoned, which is a continuation of Ser. No. 349,695, May 10, 1989, abandoned.

[30] Foreign Application Priority Data

May 11, 1988 [DE] Germany .............. 3816126

[51] Int. Cl.⁵ .............. B01F 17/16; C07C 69/34; C07C 69/80; C07C 69/82
[52] U.S. Cl. .............. 252/356; 252/351; 252/357; 106/499; 106/504; 560/88; 560/196; 528/288; 528/291
[58] Field of Search .............. 252/351, 356, 357; 106/499, 504; 528/288, 291; 560/88, 196; 554/109

[56] References Cited

U.S. PATENT DOCUMENTS

| | | | |
|---|---|---|---|
| 2,884,459 | 4/1959 | Kirkpatrick et al. | 560/88 |
| 3,200,155 | 8/1965 | Kirkpatrick et al. | 560/196 |
| 3,841,888 | 10/1974 | Belde et al. | 106/413 X |
| 3,894,070 | 7/1975 | Tomiyama et al. | 8/172 X |
| 3,916,008 | 10/1975 | Green et al. | 560/105 X |
| 3,947,287 | 3/1976 | Belde et al. | 106/413 |
| 4,026,941 | 5/1977 | Login et al. | 560/88 |
| 4,200,585 | 4/1980 | Berger et al. | 560/151 X |
| 4,414,032 | 11/1983 | Schrattenholz et al. | 106/186 |
| 4,464,203 | 8/1984 | Belde et al. | 106/413 |
| 4,659,492 | 4/1987 | Jahnke | 252/51.5 A X |
| 4,844,709 | 7/1989 | Marten | 524/377 X |
| 5,279,766 | 1/1994 | Dahms | 252/356 |

FOREIGN PATENT DOCUMENTS 2849329 5/1979 Germany .

OTHER PUBLICATIONS

Patent Abstracts of Japan, Band 8, Nr. 273 (G-256), (1984).

*Primary Examiner*—Robert L. Stoll
*Assistant Examiner*—Daniel S. Metzmaier
*Attorney, Agent, or Firm*—Connolly & Hutz

[57] ABSTRACT

According to the invention, oxyalkylates of aliphatic or cyclic, primarily primary diamines or polyamines, or block polymers (having recurring structural units of the abovementioned oxyalkylate type) produced by prior linking of such oxyalkylates with dicarboxylic acids, are converted into novel substances which are suitable for a very wide variety of areas of application in the field of interface-active agents and can be employed, for example, in the preparation of azo pigments to improve the coloristic properties, by esterification of the terminal hydroxyl group in these aminoxyalkylates using fatty acids or aromatic carboxylic acids and/or resin acids, and, if appropriate, subsequent reaction of free hydroxyl groups which are still present with dicarboxylic acids and sulfite to form the corresponding monoester (containing anionic radicals).

20 Claims, No Drawings

MODIFIED BLOCK POLYMERS, THEIR PREPARATION AND THEIR USE

This application is a continuation of now abandoned application Ser. No. 07/638,024, filed on Jan. 7, 1991, which is a continuation of the now-abandoned application Ser. No.07/349,695, filed on May 10, 1989.

The invention relates to the area of surface-active substances, which can be employed, for example, as environmentally friendly dispersants and formulation agents for producing colorant dispersions, as emulsifiers for the preparation of fatty and mineral oil emulsions, as coupling auxiliaries in the synthesis of azo pigments, and as dyeing auxiliaries, wetting agents and leveling agents.

In the preparation of formulations of colorants., in particular pigments, for use in aqueous and organic media, non-ionogenic, anion-active and also cation-active surfactants are frequently used. Due to the surface-active properties of such surfactants, the coloristic properties in the various application media in the printing sector are significantly affected. Surfactants are also usually used in the preparation of azo pigments and soluble azo dyes to improve the course of the coupling reaction.

German Auslegeschrift 1,081,226 has already disclosed surface-active polymeric compounds which are obtainable by oxypropylation and oxyethylation of aliphatic primary diamines and which are used as detergents or dispersants for lime soaps.

German Auslegeschriften 2,156,603 and 2,236,906 describe aqueous, flocculation-stable pigment dispersions which are prepared with the aid of block polymers of oxyalkylated aliphatic, aromatic or cycloaliphatic diamines.

German Offenlegungsschrift 2,260,969 mentions monocarboxylic acid esters of diaminooxyethylates and their suitability as medicaments.

In addition, Japanese Patent Disclosure Sho-59-071, 486 describes block polymers of ethylenediamine derivatives with an alkylene oxide as an auxiliary in the padding of disperse dyes on hydrophobic synthetic fibers. Finally, Japanese Patent Disclosure Sho-60-024,229 discloses styrene-modified block polymers, some of which have been sulfated using sulfuric acid, of oxyalkylated alkylenediamines for use as leveling agents in the dyeing of synthetic materials.

Structurally modified block polymers of a similar type have now been found according to the invention; when used in the areas of application mentioned in the introduction, these polymers have surface-active properties which are improved in many respects compared with the compounds of the prior art.

The present invention relates to novel compounds having the structure of a block polymer (I) which has been modified by multiple esterification, optionally in various forms, and built up, according to the formula, from a) 1 to 10, preferably up to 5, trivalent or tetravalent block oxyalkylate units based on diamines or polyamines (aminoxyalkylates) having the general formula (Ia)

$$\begin{array}{c}-(O-X)_n\\ \phantom{-(O-X)_n}\diagdown\\ \phantom{-(O-X)_n}N-A-N\\ \phantom{-(O-X)_n}\diagup\phantom{N-A-N}\diagdown\\ -(O-X)_n\phantom{N-A-N}R(-)\end{array}\diagup(X-O)_n-\quad\text{(Ia)}$$

b) monovalent acid radicals symbolized by the general formula (Ib)

$$-Z \qquad\qquad \text{(Ib)}$$

and, when two or more formula units (Ia) are present, additionally from c) divalent groups of the general formula (Ic)

$$-CO-B-CO- \qquad\qquad \text{(Ic)}$$

where each of the free valences indicated in the formula units (Ia) is defined in a manner such that it is bonded, independently of one another, directly to one formula unit (Ib) in each case or to a valence of the formula unit (Ic), and where, in the formula units (Ia) to (Ic), A represents a straight-chain, branched or cyclic aliphatic radical, an aromatic or araliphatic radical having 1 to 300 carbon atoms in each case, preferably represents $C_2$–$C_{12}$-alkylene, in particular $C_2$–$C_6$-alkylene, or $C_6$–$C_{12}$-arylene, $C_7$–$C_{14}$-alkylarylene, $C_5$–$C_7$-cycloalkylene or $C_2$–$C_{24}$-alkylene which is interrupted once or several times by a group of the formula NR' in which R' is hydrogen, $C_1$–$C_4$-alkyl or a group of the formula —(X—O)$_n$— with one free valence as defined above, or represents a combination of the divalent groups listed, X represents identical or different groups of the formulae —$CH_2CH_2$— and —$CH_2CH(CH_3)$—, where the latter formula here and below is also intended to include the formula —CH($CH_3$)$CH_2$, n represents identical or different numbers from 1 to 100, in particular 1 to 20, R represents a $C_1$–$C_3$-alkyl group or a divalent group of the formula —(X—O)$_n$— with one free valence as defined above and indicated by (—), B represents a straight-chain, branched or cyclic aliphatic radical, an aromatic or araliphatic radical having 1 to 60 carbon atoms in each case, preferably represents straight-chain $C_1$=$C_8$-alkylene an alkylene radical of a dicarboxylic acid based on dimerized $C_{11}$–$C_{24}$-fatty acids, cyclohexylene, $C_6$–$C_{12}$-arylene or a group of the formula —CH=CH— or —$CH_2CH(SO_3M)$— in which M represents a cation and the latter formula here and below is also intended to include the formula —CH($SO_3M$)$CH_2$—, and Z represents identical or different radicals $Z^1$ to $Z^6$, in which Z$^1$ denotes hydrogen, Z$^2$ denotes an acyl radical of the formula $R^1$—CO— in which $R^1$ denotes a straight-chain, saturated or unsaturated $C_7$–$C_{21}$-aliphatic hydrocarbon radical which, in addition, may be substituted by one or two hydroxyl groups or by one $C_6$–$C_{12}$-aryl or $C_6$–$C_{12}$-hydroxyaryl radical, preferably denotes an alkyl radical of a fatty acid having 12 to 18 carbon atoms, Z$^3$ denotes an acyl radical of the formula $R^2$—CO— in which $R^2$ denotes a straight-chain, branched or cyclic, saturated or unsaturated aliphatic hydrocarbon radical having 1 to 6 carbon atoms which, in addition, may be substituted by $C_6$–$C_{12}$-aryl, or denotes a phenyl or naphthyl radical or a monosubstituted to trisubstituted phenyl or naphthyl radical, the substituents being selected from the series comprising $C_1$–$C_{12}$-alkyl, $C_1$–$C_{12}$-alkoxy, sulfo, hydroxyl, amino, $C_1$–$C_{12}$-alkylamino, di-($C_1$–$C_{12}$-alkyl)amino, $C_2$–$C_5$-acylamido, acetoacetamido, aminocarbonyl, $C_1$–$C_4$-alkylaminocarbonyl and di-($C_1$–$C_4$-alkyl)aminocarbonyl, $Z^4$ denotes an acyl radical of a monofunctional resin acid of the colophonium type, $Z^5$ denotes a group of the formula $-SO_3M$ in which M denotes a cation, or an acyl radical of the formula $-CO-B-COOM$ in which B has the defined meaning and M represents a cation, and $Z^6$ denotes an acyl radical of the formula $-CO-B-COO-(X-O)_m-Y-R^3$, in which B and X have the meanings mentioned, Y is a direct bond or a group of the formula CO, m is a number from 1 to 150, preferably 1 to 50, in the case where Y=CO and a number from 0 to 150, preferably 0 to 50, in the case where Y=a direct bond, and $R^3$ is a saturated or unsaturated aliphatic, aromatic or araliphatic $C_3$–$C_{24}$-hydrocarbon radical, and $Y-R^3$ is preferably an alkyl radical of a fatty acid having 8 to 20 carbon atoms, a $C_8$–$C_{20}$-alkyl radical of a fatty alcohol, an acyl radical of a monofunctional resin acid, phenyl, naphthyl, $C_7$–$C_{20}$-alkylphenyl or $C_{11}$–$C_{24}$-alkylnaphthyl, where at least one radical Z represents a radical from the group comprising $Z^2$, $Z^4$ and $Z^6$.

Compounds of the general structure ( I ) of particular interest are those in which A represents $C_2$–$C_6$-alkylene, a group of the formula $-C_6H_{10}-(C_1-C_4$-alkylene$)-C_6H_{10}-$ or of the formula $-(C_xH_{2x}-NR')_p-C_xH_{2x}-$, in which x is 2 to 4, preferably 2, and p is 1 to 5, preferably 1 or 2, and R' denotes hydrogen, $C_1$–$C_4$-alkyl or a group of the formula $-(X-O)_n-$ having one free valence as defined above, 80 to 100% of the X represent groups of the formula $-CH_2CH_2-$, B represents $C_1$–$C_6$-alkylene, an alkylene radical of a dicarboxylic acid based on dimerized unsaturated $C_{16}$–$C_{18}$-fatty acids, 1,2-, 1,3- or 1,4-phenylene, or a group of the formula $-CH=CH-$ or $-CH_2CH(SO_3M)-$ in which M represents a cation, and Z represents identical or different radicals $Z^1$ to $Z^6$ in which $Z^1$, $Z^2$, $Z^4$ and $Z^5$ have the abovementioned meaning and $Z^3$ denotes phenyl, naphthyl, or a monosubstituted to trisubstituted phenyl or naphthyl radical, the substituents being selected from the series comprising $C_1$–$C_4$-alkyl, $C_1$–$C_4$-alkoxy, hydroxyl, amino, acetamido or acetoacetamido, and $Z^6$ denotes an acyl radical of the formula $-CO-B-COO-(X-O)_m-Y-R^3$ in which X, Y and B have the above-defined meaning, and m is 1 to 50, preferably 1 to 20, and $-Y-R^3$ is an acyl radical of a $C_{12}$–$C_{18}$-fatty acid, phenyl, naphthyl, $C_7$–$C_{18}$-alkylphenyl, $C_{11}$–$C_{22}$-alkylnaphthyl or an acyl radical of a monofunctional resin acid of the colophonium type, where at least one radical Z has the meaning of $Z^2$, $Z^4$ or $Z^6$.

Particularly preferred compounds of the general structure (I) are those in which more than 25%, in particular at least 50%, of the Z are selected from radicals of the formulae $Z^2$, $Z^3$, $Z^4$, $Z^5$ and $Z^6$.

The invention also relates to a process for the preparation of the compounds having the structure (I) according to the invention, which comprises reacting some or all of the diamine oxyalkylates of the formula (Ia) in which the free valences are saturated by $Z^1$=hydrogen, with compounds of the formula H-Z where Z has one or more of the abovementioned meanings $Z^2$ to $Z^6$ and at least one thereof has the meaning $Z^2$, $Z^4$ or $Z^6$, in one or more steps with esterification.

The aminoxyalkylates (block polymers) of the formula (Ia) used for the process according to the invention can be prepared by customary methods from diamines or polyamines by reaction with ethylene oxide and/or propylene oxide, or are in many cases commercially available as such. Preferred block polymers are based on aliphatic or cycloaliphatic diamines and polyamines, such as, for example, 1,2-diaminoethane, 1,3-diaminopropane, 1,2diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,12-diaminododecane, in particular the diamines mentioned having an even number of carbon atoms, and 1,3-diaminopropane and 1,5-diaminopentane, or mixtures thereof, and bis-(4aminocyclohexyl)methane, 1,1-bis-(4-aminocyclohexyl)ethane, 2,2-bis-(4-aminocyclohexyl)propane, diethylenetriamine, dipropylenetriamine, triethylenetetramine, dipropylenetetramine, tetraethylenepentamine, 2-methylaminoethylamine, 2-ethylaminoethylamine, 3-methylaminopropylamine, N-methyldipropylenetriamine or mixtures thereof.

The oxyalkylation of the amines for the preparation of the base block polymers (Ia) is carried out by customary methods, preferably using alkali metal hydroxides or alkoxides as catalyst, at 100°–200° C., in particular at 140°–180° C. The amount of ethylene oxide or propylene oxide or of a mixture of the two epoxides is such that the ability to form a stable emulsion or complete solubility in water of the base block polymers formed is preferably achieved. Expediently, 1 to 150, preferably 1 to 50, in particular 5 to 25, molecules of epoxide are employed for each reactive position in the diamine molecule, i.e. per hydrogen atom of the primary and secondary amino groups present. The amount of alkylene oxide adducted is also appropriate to the intended use and thus to the intended degree of hydrophilicity.

A suitable alkali metal hydroxide is potassium hydroxide or preferably sodium hydroxide, and a suitable alkali metal alkoxide is sodium methoxide or ethoxide. The concentration of the alkaline catalysts should preferably be 0.05–1.0% by weight, based on the amine, on commencement of the oxyalkylation. The oxyalkylation can be carried out without pressure or in pressure vessels with propylene oxide or preferably with ethylene oxide or mixtures of the two, it being possible to supply the alkylene oxide in gas form or in liquid form. The operating pressure is generally 1–10 bar, preferably 2–4 bar.

The actual reaction to produce the block polymers, modified according to the invention, of the general structure (I) from the base block polymers (Ia) is generally carried out in one or more reaction steps, the introduction of the radicals Z with the meaning $Z^2$, $Z^3$, $Z^4$ and $Z^5$ generally being carried out through reaction with appropriate carboxylic acids of the formula $R^1$—COOH, $R^2$—COOH, resin acids or dicarboxylic acids of the formula HOOC-B-COOH or the anhydrides thereof.

For example, some or all of the hydroxyl groups of the oxyalkylated amino compounds (base block polymers) can be esterified in this way using the abovementioned carboxylic acids. It is likewise possible to employ mixtures of such carboxylic acids. In general, it is advantageous to use monofunctional carboxylic acids in a first reaction step to esterify some of the hydroxyl groups present, and then to esterify with dicarboxylic acids in a second reaction step, anionic radicals of the free carboxylate group type being introduced in the second reaction step, depending on the amount of dicarboxylic acid used, or, in particular when less than the stoichiometric amount of dicarboxylic acid is used, crosslinking of the base molecules via the dicarboxylic acids takes place.

Examples of suitable dicarboxylic acids of the formula $R^1$—COOH are saturated or unsaturated carboxylic acids or hydroxycarboxylic acids having 8 to 22 carbon atoms, such as, for example, octanoic acid, pelargonic acid, capric acid, undecanoic acid, lauric acid, tridecanoic acid, myristic acid, pentadecanoic acid, palmitic acid, heptadecanoic acid, stearic acid, nonadecanoic acid, arachidonic acid, behenic acid, 10-undecenoic acid, lauroleic acid, myristoleic acid, palmitoleic acid, 6c- and 6t-octadecenoic acid, elaidic acid, oleic acid, linoleic acid, linolenic acid, ricinoleic acid or ricinenic acid, in particular even-numbered fatty acids or hydroxyfatty acids, in each case having 8 to 20 carbon atoms, for example the even-numbered fatty acids correspondingly mentioned above, and, in particular, mixtures thereof obtained from natural products, such as tall oil fatty acid, tallow fatty acid, coconut oil, palm oil fatty acid, linseed oil fatty acid, castor oil fatty acid and ricinenic acids, preferably the fatty acids mentioned having 12 to 18 carbon atoms; furthermore, suitable are modified fatty acids and mixtures thereof, as obtainable by Friedel-Crafts reaction of aromatic hydroxyl compounds, for example phenol, o-, m-and p-cresol, guayacol, salicylic acid, α-naphthol or β-naphthol, with unsaturated fatty acids, such as palmitoleic acid, oleic acid, undecyl acid and ricinoleic acid, in the presence of strongly acidic or acid-eliminating catalysts, such as, for example, boron trifluoride, aluminum chloride, p-toluenesulfonic acid, methanesulfonic acid, mineral acids or ion exchangers, at temperatures between 50 and 200° ωC., preferably 120°-160° C., if appropriate in an organic medium, 0.5-1.1 moles, preferably 0.9-1 mole, of the unsaturated fatty acids being used per mole of the phenols or naphthols mentioned Examples of suitable carboxylic acids $R^2$—COOH are monocarboxylic acids having 2 to 6 carbon atoms, such as acetic acid, propionic acid, butyric acid, valeric acid, capric acid and heptanoic acid, furthermore aromatic carboxylic acids, such as benzoic acid, anthranilic acid, p-aminobenzoic acid, salicylic acid, o-, m- and p-tolyl acids, -methoxy- and -ethoxybenzoic acids, -acetoacetamidobenzoic acids and, -acetamidobenzoic acids, phenylacetic acid or naphthoic acids, in particular oxynaphthoic acids, for example 3-hydroxy-1-naphthoic acid, 3-hydroxy-2-naphthoic acid, 4-hydroxy-2-naphthoic acid, 5-hydroxy-1-naphthoic acid, 5-hydroxy-2-naphthoic acid, 6-hydroxy-2-naphthoic acid and 7-hydroxy-2-naphthoic acid.

Suitable carboxylic acids $Z^4$—H are unmodified or modified natural resin acids of the colophonium type or reactive derivatives thereof, preferably resin acids such as abietic acid, dehydroabietic acid, tetrahydroabietic acid, laevopimaric acid, dextropimaric acid or isodextropimaric acid, as present in commercially available colophonium grades, and modified resin acids- such as disproportionated, hydrogenated and dimerized natural resin acids.

To introduce the groups $Z^6$, the base diaminoxyalkylate (Ia) or partially esterified diaminoxyalkylates can be esterified using carboxylic acids of the defined formula HOOC—B—COO—(X—O)$_m$—Y—$R^3$, carboxylic acids of this being accessible, in particular, from fatty alcohols or adducts of ethylene oxide and/or propylene oxide with fatty acids, fatty alcohols, phenols, naphthols, alkylphenols or alkylnaphthols by esterification using dicarboxylic acids. It is also possible, as mentioned below, to first introduce anionic groups into the base oxyalkylate by semi-esterification using the dicarboxylic acids and then to react the free carboxyl groups with fatty alcohols, oxyalkylated fatty acids or oxyalkylated fatty alcohols.

The linking of several block polymer units of the formula (Ia) can be carried out by reacting the base block polymers in a first reaction step through esterification using one or more dicarboxylic acids of the formula HOOC—B—COOH in the molar ratio from 2:1 to 10:9, preferably 2:1 to 5:4. Suitable dicarboxylic acids for linking are preferably aliphatic dicarboxylic acids having 3-12 carbon atoms, in particular malonic acid, succinic acid, glutaric acid, adipic acid, 1,5-pentanedicarboxylic acid, 1,6-hexanedicarboxylic acid or 1,10-decanedicarboxylic acid, but also, for example, cyclohexane-1,4-dicarboxylic 20 acid and aromatic dicarboxylic acids such as phthalic acid or terephthalic acid.

In place of the carboxylic acids, the anhydrides or reactive carboxylic acid derivatives, if present, can also be employed for the esterification, for example in the case of transesterification reactions another esters of the carboxylic acids.

The linking according to the invention of two or more block polymer units which have already been esterified on part of the polyglycol ether chains in the terminal position with monocarboxylic acids can preferably be carried out in a second reaction step by esterification using the abovementioned dicarboxylic acids, a block polymer:dicarboxylic acid ratio of from 2:1 to 10:9 again being preferably selected, apart from the case in which the partially esterified base block polymer only has one free hydroxyl group. In the last-mentioned case, only a molar ratio of about 2:1 is appropriate.

However, it is also possible to carry out the reaction of the base block polymers with monocarboxylic acids and dicarboxylic acids in one reaction step, in which case mixtures of polynuclear and mononuclear esterified block polymers are generally produced.

The esterification of the base block polymers (Ia) using the monocarboxylic acids or dicarboxylic acids can be carried out by esterification methods which are customary per se. The reaction temperature to be maintained here is generally between room temperature and 240° C., depending on the esterification method. In order to increase the yield, the esterification is preferably carried out in an inert organic solvent which is suitable as an entrainer to remove the water of reaction. For example, the esterification can be carried out in xylene as the organic solvent and in the presence of acidic catalysts at a temperature of 130°–220° C. Examples of possible acidic catalysts are acids and Lewis acids, such as benzenesulfonic acid, p-toluenesulfonic acid, boric acid, tin powder, zinc chloride or sulfuric acid.

Alternatively, the esterification of the base block polymers can also be carried out by transesterification using the appropriate alkyl esters, preferably methyl esters, of the monocarboxylic acids or dicarboxylic acids mentioned, usually in the presence of catalysts, preferably in the presence of 0.1–1.0 times the molar amount of an alkoxide per mole of ester, preferably sodium methoxide, at 150–200° C., in particular 160–190° C., while removing the liberated alkanol or methanol by distillation. The esterified block polymers obtained in the first or second reaction step are valuable surface-active agents as such and can be employed in the context of the invention.

In order to introduce anionic groups, the base block polymers or the block polymers which have been partially esterified using monocarboxylic acids, so long as the latter still have free hydroxyl groups, can be reacted, for example, with sulfuric acid, amidosulfonic acid or chlorosulfonic acid or the corresponding anhydrides, with sulfato groups being introduced. According to another variant, the base block polymers or the partially esterified block polymers are reacted with an excess of dicarboxylic acids or anhydrides thereof to form the corresponding monoesters. Suitable dicarboxylic acids are the abovementioned dicarboxylic acids of the formula HOOC—B—COOH which are suitable for crosslinking the block polymer units of the formula (Ia) and the anhydrides thereof.

The anionic groups are preferably converted by reaction with maleic anhydride or phthalic anhydride by mixing and stirring at 20°–100° C., preferably at 40°–80° C., in the presence of alkali metal hydroxides. The concentration of the alkali metal hydroxides should preferably be 0.1–1.0% by weight, based on the overall mixture. In the case of maleic anhydride, it is advantageous, due to the tendency towards sublimation, to carry out the reaction in pressure vessels under an excess pressure of 0.2–1 bar of nitrogen or air and to ensure vigorous mixing, since the molten maleic anhydride is not very miscible with the partially esterified oxyalkylates at the beginning of the reaction.

In the case where maleic acid monoester groups are introduced, it is also advantageous to convert these monoester groups into the corresponding sulfosuccinic acid monoester groups. This is carried out, for example, by adding aqueous solutions of sulfites or bisulfites to the compounds which contain maleic acid monoester groups 1.0–1.5 moles, preferably 1.0–1.1 moles, of sulfurous acid in the form of alkali metal or alkaline earth metal sulfites or bisulfites or pyrosulfites are employed per mole of maleic acid monoester groups. The reaction is generally carried out in the presence of about 50–85% of water, based on the overall solution or mixture. The amount of water depends on the solubility of the underlying sulfosuccinic acid monoester salts and on the viscosity of the solutions. The reaction temperature during the reaction of sulfites with the maleic acid monoester compounds is generally 20–100° C., in particular 40°–80° C.

While the sulfites are particularly suitable for the formation of the dialkali metal salts of sulfosuccinic acid monoesters, it is possible, during the addition reaction of bisulfites, to additionally influence the degree of hydrophilicity by neutralization using bases such as ammonia, low-molecular-weight alkylamines or alkylolamines or of corresponding alkylene oxide adducts, up to about 150 moles of ethylene oxide or propylene oxide or both alkylene oxides being adducted per mole of amine or alkylolamine and up to 150, preferably 5–30, molecules of ethylene oxide or propylene oxide or both being adducted per reactive hydrogen atom of the compounds mentioned. Representatives of alkylamines or alkylolamines which may be mentioned are: ethylamine, propylamine, isopropylamine, butylamine, isobutylamine, monoethanolamine, monopropanolamine, monoisopropanolamine, monobutanolamine, monoisobutanolamine, diethanolamine, dipropanolamine, dibutanolamine, triethanolamine, tripropanolamine or tributanolamine, and diamines and polyamines such as ethylenediamine, ethylenetriamine, triethylenetetramine, propylenediamine, dipropylenediamine, dipropylenetriamine or tripropylenetetramine.

The cation exchange described using the example of sulfosuccinic acid monoester groups can also be carried out in the case of the compounds of the structure (I) which contain other anionic groups. In this case, the compounds are employed in their acid form and converted into the appropriate salts in an analogous manner by neutralization using the abovementioned amines or inorganic bases. It is also possible to use other customary cation exchange methods.

Whereas the ammonium salts of sulfuric acid monoester are produced in the case of sulfation using amidosulfonic acid, sulfuric acid monoesters in the acid form, from which the desired salts can easily be prepared by neutralization using appropriate inorganic or organic bases, are produced in the case of the industrially interesting embodiment using gaseous sulfur trioxide mixed with an inert gas and in the case of sulfation using chlorosulfonic acids. For this neutralization, the alkali metal hydroxides, which result in the extremely water-soluble alkali metal salts of the sulfuric acid monoesters according to the invention, are preferably employed.

In a further reaction step, it is possible to react modified block polymers which still contain anionic radicals in the form of carboxylate radicals into modified block polymers by reaction with alcohols of the formula HO—(X—O)$_m$—Y—R$^2$ in which Z has the abovementioned meaning of Z$^6$. This esterification reaction can be carried out analogously to the esterifications already mentioned above.

The compounds according to the invention have a wide range of advantageous properties. They belong to the class of surface-active compounds in accordance with DIN 53900, reduce the surface tension by the ring separation method (DIN 53914) and, according to the results in the modified Ross-Miles test (DIN 53902), can be regarded as non-foaming or low-foaming surface-active substances. At a suitable degree of hydrophilicity, they exhibit an excellent wetting capacity for cotton by the dip-wetting method (DIN 53901) and at the same time a good leveling behavior in accordance with DIN 53504. They have a very good flocculation-protection capacity towards pigments and dyes (DIN 53908) and a very good water-distribution action as cleaning promoters (DIN 53980) and are easy to wash out as fluxes (DIN 53504). The products are biodegradable.

Due to their wide variety of surface-active properties, the substances according to the invention can be employed for a broad range of applications.

The invention therefore also relates to the use of the compounds of the abovementioned structure (I) as surface-active agents. Of particular interest is the use for employment as a coupling auxiliary and emulsifier in the preparation of azo colorants, in particular azo pigments, as a dispersant and distribution agent for the fine distribution and stabilization of sparingly soluble or insoluble colorants, preferably for the preparation of pigmented dispersions with good flow properties for the aqueous printing inks sector or for the preparation of formulations of dispersion dyes, as are preferably used for the dyeing of natural and synthetic fiber materials, such as cotton, wool, cellulose, viscose staple fiber, cellulose acetate, cellulose triacetate, polyester, nylon and polyacrylonitrile, or of fiber materials which contain these materials. The substances according to the invention are suitable as additives and emulsifiers, such as, for example, as corrosion-protection additives, as additives for the preparation of cooling lubricants and cold rolling oils in the metalworking industry. In addition the substances can be used as dispersants and emulsifiers for the preparation of cleaning promoters, carrier emulsions and formulations for crop protection agents and pesticides. They are likewise suitable as wetting agents and leveling agents in dyeing.

The compounds can be used individually, as mixtures or in combination with other non-ionogenic, anion-active and/or cation-active surfactants, builders and other customary additives or auxiliaries.

The examples below serve to illustrate the invention in greater detail. Parts and percentages relate to the weight, pressure data are excess pressure, relative to atmospheric pressure, unless otherwise stated. Parts by volume are to parts by weight as the liter is to the kilogram.

In order to characterize the compounds prepared, the hydroxyl number or the acid number is indicated in several examples. The hydroxyl number is the amount of KOH, in mg, which is necessary to neutralize the amount of acetic acid consumed on acetylation of 1 g of the compound. The acid number is the amount of KOH, in mg which is required to neutralize 1 g of the compound.

PREPARATION EXAMPLES

1a) Diaminoethane +32 EO 50 parts of 1,2-diaminoethane are oxyethylated with stirring and supply of 1,173 parts of ethylene oxide (EO) without addition of a catalyst while maintaining a pressure of 2-4 bar at an initial temperature of 80° C. and a final temperature of 140° C. When all the ethylene oxide has been injected into the reaction vessel, the mixture is stirred for a further hour at 130°-140° C. The product obtained has a hydroxyl number of 155.

1b) Ester of 1a) with 3 mole equivalents of tallow fatty acid 146.8 parts of the oxyethylate 1a) are warmed to 70°-80° C. with 83.7 parts of commercially available tallow fatty acid, and the mixture is stirred under nitrogen gas for 1 hour. After 1.5 parts of p-toluenesulfonic acid and 150 parts of xylene have been added, the mixture is heated at 150°-160° C. for 16 hours, during which period the water of reaction is removed from circulation on a water separator. The xylene is then removed by distillation, and the acid number is determined in accordance with DIN 53185. The product has an acid number of less than 20.

2) Ester of 1a) with 2 mole equivalents of colophonium 440.4 parts of the oxyethylate 1a) are warmed to 70°-80° C. with 181.2 parts of disproportionated colophonium, and the mixture is stirred under nitrogen gas for 1 hour. After 12 parts of tin powder, 4.0 parts of p-toluenesulfonic acid and 150 parts by volume of xylene have been added, the mixture is stirred at 150°-160° C. for 16 hours and the water of reaction is removed from circulation. After the xylene has been removed by distillation, a product having an acid number of less than 25 is obtained.

Mixed ester of 1a) with 2 mole equivalents of tallow fatty acid and 2 mole equivalents of phthalic acid (monoester)

146.8 parts of the oxyethylate 1a) are esterified to an acid number of 16 analogously to 1b) using 55.8 parts of commercially available tallow fatty acid, and subsequently reacted with 29.6 parts of phthalic anhydride at 80°-90° C. over the course of 5 hours in the presence of 0.2 part of powdered caustic soda. The pH is subsequently adjusted to 6.8-7.0 by adding a solution of 440 parts of water and 16 parts of caustic soda. The amount of water added is preferably between 50 and 85% of the finished product solution.

4) Mixed ester based on 1a), 2 mole equivalents of tallow fatty acid and 2 mole equivalents of sulfosuccinic acid monoester groups 146.8 parts of the oxyethylate 1a) are esterified to an acid number of less than 15 analogously to compound 1b) using 83.7 parts of commercially available tallow fatty acid, and subsequently esterified at 70°-80° C. over the course of 4 hours using 19.2 parts of maleic anhydride in the presence of 0.1 part of powdered caustic soda, and subsequently converted into the sulfosuccinate by adding a solution of 24.7 parts of sodium sulfite in 508 parts of water.

5a) Diaminoethane +4 PO +24 EO 50 parts of 1,2-diaminoethane are oxyalkylated at 90°-110° C. with stirring and supply of 183.3 parts of propylene oxide (PO), and, after 3 parts of sodium methoxide have been added and the methanol has been removed under reduced pressure, is reacted with 879.6 parts of ethylene oxide at 3-5 bar and at 120°-140° C. The product obtained has a hydroxyl number of about 163.

5b) Ester of 5a) and 2 mole equivalents of ricinenic acid and 2 mole equivalents of phthalic acid 137.8 parts of the oxyalkylate 5a) were esterified to an acid number of less than 18 analogously to compound 1b) using 56 parts of commercially available ricinenic fatty acid, and subsequently reacted at 80°-90° C. over the course of 5 hours with 29.6 parts of phthalic anhydride in the presence of 0.2 parts of powdered caustic soda. A pH of 6.8-7.0 is set by adding a solution of 764 parts of water and 188.2 parts of an adduct of triethanolamine and 18 mole equivalents of ethylene oxide.

6) Ester of 5a) and 1 mole equivalent of tall oil fatty acid and 1 mole equivalent of 2-acetoacetamidobenzoic acid 137.8 parts of the oxyethylate 5a) are esterified to an acid number of less than 20 in corresponding manner to 1b) using 28.2 parts of commercially available tall oil fatty acid, but the xylene is not removed by distillation at the end. Analogously to the previous esterification, the mixture is esterified to an acid number of less than 25 by adding a further 0.5 part of p-toluenesulfonic acid and 22.1 parts of 2-(acetoacetamido)benzoic acid, and the xylene is removed by distillation at the end of the esterification.

7a) Oxyethylate of diaminoethane +8 PO +60 EO 50 parts of 1,2-diaminoethane are oxyalkylated analogously to 5a) using 387 parts of propylene oxide and 2,200 parts of ethylene oxide at 2–4 bar in the temperature range 80°–140° C. Towards the end of the reaction, the mixture is stirred for a further 1 hour at 135°–140° C. The product has a hydroxyl number of about 71.

7b) Ester of 7a) and 1 mole equivalent of tallow fatty acid and 1 mole equivalent of 2-hydroxy-3-naphthoic acid 300 parts of the oxyalkylate 7a) are esterified to an acid number of less than 10 in corresponding manner to compound 1b) using 25.5 parts of a commercially available tallow fatty acid in xylene. After a further 0.7 part of p-toluenesulfonic acid and 17.8 parts of 2-hydroxy-3naphthoic acid have been added, the mixture is esterified 10 to an acid number of less than 20 while removing the water of reaction from circulation. The xylene is subsequently removed by distillation.

Ester of 7a) and 1 mole equivalent of colophonium and 1 mole equivalent of 2-hydroxy-6-naphthoic acid 300 parts of the oxyalkylate 7a) are esterified to an acid number of less than 20 in corresponding manner to compound 2) using 28.7 parts of commercially available disproportionated colophonium in xylene. The mixture is esterified further to an acid number of less than 18 analogously to compound 7b) after 0.5 part of p-toluenesulfonic acid and 17.8 parts of 20-hydroxy-6-naphthoic acid have been added, and the xylene is subsequently removed by distillation.

9a) Diaminopropane +4 PO +32 EO 50 parts of 1,3-diaminopropane are oxypropylated at 90°–110° C. analogously to compound 5a) using 156.8 parts of propylene oxide, and, after 2 parts of sodium methoxide have been added, the methanol produced is removed under reduced pressure. The mixture is subsequently reacted with 951.3 parts of ethylene oxide at 2–4 bar and at 120°–140° C. The oxyalkylate obtained has a hydroxyl number of about 131.

9b) Ester of 9a) and 1 mole equivalent of tallow fatty acid and 1 mole equivalent of colophonium 300 parts of 9a) are esterified at 155°–165° C. over the course of 16 hours while removing the water of reaction from circulation, using 47.5 parts of commercially available tallow fatty acid and 59.8 parts of disproportionated colophonium after 6 parts of tin powder, 1.5 parts of p-toluenesulfonic acid and 150 parts by volume of xylene have been added. After the xylene has been removed by distillation, a product is obtained which has an acid number of less than 20.

10a) Oxyalkylate of diethylenetriamine +10 PO +40 EO 50 parts of diethylenetriamine are reacted analogously to compound 6a) with 281.3 parts of propylene oxide and, after 2.5 parts of sodium methoxide have been added and the methanol has been removed under reduced pressure, with 853.3 parts of ethylene oxide. The product has a hydroxyl number of about 115.

10b) Ester of 10a) and 3 mole equivalents of tall oil fatty acid.

500 parts of the oxyalkylate 10a) are esterified at 155°–160° C. 160° C. over the course of 12 hours as in the case of compound 1b) using 173 parts of commercially available tall oil fatty acid after 3 parts of boric acid and 200 parts of xylene have been added. After the xylene has been removed by distillation, a product having an acid number of less than 18 is obtained.

11) Ester based on 10a) and 2 mole equivalents of tall oil fatty acid and 2 mole equivalents of sulfosuccinic acid monoester groups 300 parts of the ester 10b) are esterified at 70°–80° C. over the course of 4 hours using 24 parts of maleic anhydride in the presence of 0.1 part of powdered caustic soda, and reacted at 75°–85° C. over the course of 3 hours by adding a solution of 30.9 parts of sodium sulfite in 657 parts of water.

12a) Bis-(4-aminocyclohexyl)methane +40 EO 103 parts of bis-(4-aminocyclohexyl)methane are reacted as in the case of Example 5a) with 116 parts of propylene oxide and, after 2 parts of sodium methoxide have been added, with 870 parts of ethylene oxide. The product obtained has a hydroxyl number of 105.

12b) Ester of 12a) and 2 mole equivalents of tallow fatty acid 500 parts of the oxyalkylate 12a) are esterified at 155°–165° C. over the course of 15 hours analogously to Example 1b) using 123.5 parts of commercially available tallow fatty acid after 3 parts of p-toluenesulfonic acid and 200 parts by volume of xylene have been added. After the xylene has been removed by distillation, a product is obtained which has an acid number of less than 15.

13) Ester based on 12a) and 2 mole equivalents of tallow fatty acid and 2 mole equivalents of sulfosuccinic acid monoester groups 300 parts of 12b) are esterified at 70°–80° C. over the course of 3 hours using 28 parts of maleic anhydride in the presence of 0.1 part of powdered caustic soda, and reacted at 75°–85° C. over the course of 3 hours by adding a solution of 34.7 parts of sodium sulfite in 674 parts of water.

14) Ester based on malonic acid and 3 mole equivalents of 5a)

600 parts of the oxyalkylate 5a) are warmed at 70°–80° C. under nitrogen gas with 30.9 parts of malonic acid. After 3 parts of p-toluenesulfonic acid and 200 parts by volume of xylene have been added, the mixture is heated at 155°–165° C. for 10 hours, and the water of reaction is removed from circulation. After the xylene has been removed by distillation, the product has an acid number of less than 10, a hydroxyl number of about 106 and contains 12 propylene oxide units and 72 ethylene oxide units per molecule.

15) Ester of 14) and 8 mole equivalents of oleic acid 300 parts of the oxyalkylate 14) are esterified at 155°-165° C. over the course of 18 hours analogously to 1b) using 159 parts of commercially available oleic acid after 2.1 parts of p-toluenesulfonic acid and 150 parts by volume of xylene have been added. After the xylene has been removed by distillation, a product is obtained which has an acid number of less than 25.

16) Ester based on 14) and 4 mole equivalents of oleic acid and 4 mole equivalents of sulfosuccinic acid monoester groups 300 parts of compound 14) are esterified to an acid number of less than 10 analogously to 1b) using 80 parts of commercially available oleic acid. The mixture is subsequently esterified further at 70°-80° C. over the course of 3 hours using 27.7 parts of maleic anhydride in the presence of 0.1 part of powdered caustic soda, and subsequently converted into the sulfosuccinic acid monoester by adding a solution of 35.6 parts of sodium sulfite in 824 parts of water.

17) Polyblock polymer based on malonic acid and 5 mole equivalents of 5a)

600 parts of the oxyalkylate 5a) are esterified to an acid number of less than 8 analogously to Example 14) using 37 parts of malonic acid. The product has a hydroxyl number of about 100.

18) Ester of 17) with 4 mole equivalents of tallow fatty acid and 4 mole equivalents of colophonium 300 parts of compound 17) are esterified at 155°-165° C. over the course of 16 hours analogously to compound 1b) using 45 parts of commercially available tallow fatty acid and 25.3 parts of disproportionated colophonium after 6 parts of tin powder and 2 parts of p-toluenesulfonic acid and 150 parts by volume of xylene have been added. After the xylene has been removed by distillation, the product has an acid number of less than 20.

19) Ester based on 17) and 4 mole equivalents of tallow fatty acid and 3 mole equivalents of benzoic acid and 5 mole equivalents of sulfosuccinic acid mono ester groups 300 parts of compound 17) are esterified at 155°-165° C. in 12 hours analogously to compound 1b) using 45.5 parts of commercially available tallow fatty acid and 21.0 parts of benzoic acid after 2 parts of tin powder and 150 parts by volume of xylene have been added. After the xylene has been removed by distillation, the product has an acid number of less than 25. The mixture is subsequently esterified further at 70°-80° C. over the course of 3-4 hours in the presence of 0.1 part of powdered caustic soda and 16.4 parts of maleic anhydride, and subsequently converted into the sulfosuccinic acid monoester by adding a solution of 21.1 parts of sodium sulfite.

20a) Ester based on adipic acid and 2 mole equivalents of compound 7a)

600 parts of the oxyalkylate 7a) are esterified to an acid number of less than 14 in corresponding manner to Example 14) using 13.8 parts of adipic acid. The polyblock polymer obtained has a hydroxyl number of about 53 and contains 16 propylene oxide units and 120 ethylene oxide units per molecule.

20b) Ester of 20a) and 4 mole equivalents of colophonium 300 parts of compound 20a) are esterified at 155-165° C. over the course of 18 hours with removal of the water of reaction from circulation, using 55.8 parts of commercially available colophonium after 8 parts of tin powder and 1.5 parts of p-toluenesulfonic acid and 150 parts by volume of xylene have been added. After the xylene has been removed by distillation, a product is obtained which has an acid number of less than 30.

21a) 1,2-Diaminoethane +8 PO +48 EO 1,2-Diaminoethane are oxyalkylated at 90 to 140° C. and 3 to 5 bar with stirring analogously to Example 5a) with supply of 386.6 parts of propylene oxide and 1,760 parts of ethylene oxide. The product obtained has a hydroxyl number of about 85.

21b) Ester of 21a) with 1 mole equivalent of dimeric fatty acid 500 parts of the oxyalkylate 21a) are refluxed at 150 to 160° C. for 16 hours with removal of the water of reaction from circulation with 145 parts of a commercially available dimerized fatty acid containing about 22% by weight of trimerized fatty acid, after 200 ml of xylene and 5 parts of p-toluenesulfonic acid have been added. After the xylene has been removed by distillation, an acid number of less than 30 is obtained.

We claim:

1. A compound having the structure of a modified block polymer (I), built up, corresponding to the formula, from a) 1 to 10 trivalent or tetravalent block oxyalkylate units based on diamines (aminoxyalkylates) having the general formula (Ia)

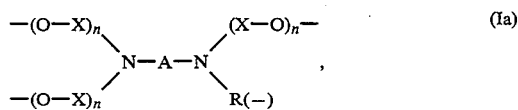

b) monovalent acid radicals symbolized by the general formula (Ib)

and, when two or more formula units (Ia) are present, additionally from c) divalent groups of the general formula (Ic)

where each of the free valences indicated in the formula units (Ia) is defined in a manner such that it is bonded, independently of one another, directly to one formula unit (Ib) in each case or to a valence of the formula unit (Ic), and where, in the formula units (Ia) to (Ic), A represents $C_2$-$C_{12}$-alkylene, $C_6H_{10}$-($C_1$-$C_4$alkylene)-$C_6H_{10}$, $C_6$-$C_{12}$-arylene, $C_7$-$C_{14}$-alkylarylene, $C_5$-$C_7$-cycloalkylene, $C_2$-$C_{24}$-alkylene or represents a combination of the divalent groups listed and, X represents identical or different groups of the formulae —$CH_2CH_2$— or —$CH_2CH(CH_3)$—, n represents identical or different numbers from 1 to 100, R represents a $C_1$-$C_3$-alkyl group or divalent group of the formula —(X—O)$_n$— with one free valence as defined above and indicated by (—), B represents a straight-chain C$_1$-C$_8$-alkylene, an alkylene radical of a dicarboxylic acid based on dimerized C$_{11}$-C$_{24}$-fatty acids, cyclohexylene, C$_5$-C$_{12}$-arylene or a group of the formula —CH=CH— or —CH$_2$CH(SO$_3$M)— in which M is a cation, Z represents identical or different radicals Z$^1$ to Z$^6$, in which Z$^1$ denotes hydrogen, Z$^2$ denotes an acyl radical of the formula R$^1$—CO— in which R$^1$ denotes a straight-chain, saturated or unsaturated C$_7$-C$_{21}$-aliphatic hydrocarbon radical which, in addition, is unsubstituted or substituted by one or two hydroxyl groups or by one C$_5$-C$_{12}$-aryl or C$_6$-C$_{12}$-hydroxyaryl radical, Z$^3$ denotes an acyl radical of the formula R$^2$—CO— in which R$^2$ denotes a straight-chain, branched or cyclic, saturated or unsaturated aliphatic hydrocarbon radical having 1 to 6 carbon atoms which, in addition, is unsubstituted or substituted by C$_6$-C$_{12}$-aryl, or denotes a phenyl or naphthyl radical or a monosubstituted to trisubstituted phenyl or naphthyl radical, the substituents being selected from the series consisting of C$_1$-C$_{12}$-alkyl, C$_1$-C$_{12}$-alkoxy, sulfo, hydroxyl, amino, C$_1$-C$_{12}$-alkylamino, di-(C$_1$-C$_{12}$-alkyl)amino, C$_2$-C$_5$-acylamido, aceto-acetamido, aminocarbonyl, C$_1$C$_4$-alkylaminocarbonyl and di-(C$_1$-C$_4$-alkyl)aminocarbonyl, Z$^4$ denotes an acyl radical of a monofunctional resin acid of the colophonium type, Z$^5$ denotes an acyl radical of the formula —CO—B—COOM in which B has the defined meaning and M represents a cation, and Z$^6$ denotes an acyl radical of the formula —CO—B—COO—(X—O)$_m$—Y—R$^3$, in which B and X have the meanings mentioned, Y is a direct bond or a group of the formula CO, m is a number from 1 to 150 in the case where Y=CO and a number from 0 to 150 in the case where Y=a direct bond, and R$^3$ is a saturated or unsaturated aliphatic, aromatic or araliphatic C$_3$-C$_{24}$-hydrocarbon radical;

wherein two or more radicals Z represent a combination of Z$^2$ with one or more of the radicals Z$^3$, Z$^4$, or Z$^6$; or a combination of Z$^5$ with Z$^3$, Z$^4$ or Z$^6$ or a combination of Z$^4$ with Z$^3$.

2. A compound as claimed in claim 1, wherein A is a C$_2$-C$_6$-alkylene or a group of the formula —C$_6$H$_{10}$—(C$_1$-C$_4$-alkylene )—C$_6$H$_{10}$—, 80 to 100% of the X represent groups of the formula —CH$_2$CH$_2$—, B is a C$_1$-C$_6$-alkylene, an alkylene radical of a dicarboxylic acid based on dimerized unsaturated C$_{16}$-C$_{18}$-fatty acids, 1,2-, 1,3- or 1,4-phenylene, or a group of the formula —CH=CH— or —CH$_2$CH(SO$_3$M)— in which M is a cation, and n is 1 to 20.

3. A compound as claimed in claim 1, wherein Z$^2$ is an alkyl radical of a fatty acid having 12 to 18 carbon atoms.

4. A compound as claimed in claim 1, wherein Z$^3$ is phenyl, naphthyl, or a monosubstituted to trisubstituted phenyl or naphthyl radical, wherein the substituents being selected from the series consisting of C$_1$-C$_4$-alkyl, C$_1$-C$_4$-alkoxy, hydroxyl, amino, acetamido or acetoacetamido.

5. A compound as claimed in claim 1, wherein Z$^5$ is an acyl radical of the formula —CO—B—COOM in which B is a group of the formula —CH$_2$—CH(SO$_3$M)— or —C$_6$H$_4$—, and M is a cation.

6. A compound as claimed in claim 1, wherein Z$^6$ is an acyl radical of the formula —CO—B—COO—(X—O)$_m$—Y—R$^3$, in which B and X have the meanings mentioned, Y is a direct bond or a group of the formula CO, m is a number from 1 to 50 in the case where Y=CO and a number from 0 to 50 in the case where Y=a direct bond, and Y—R$^3$ is an alkyl radical of a fatty acid having 8 to 20 carbon atoms, a C$_8$-C$_{20}$-alkyl radical of a fatty alcohol, an acyl radical of a monofunctional resin acid, phenyl, naphthyl, C$_7$-C$_{20}$-alkylphenyl or C$_{11}$-C$_{24}$-alkylnaphthyl.

7. A compound as claimed in claim 1, wherein there are at least two trivalent or tetravalent block oxyalkylate units based on diamines of the general formula Ia.

8. The compound as claimed in claim 1, wherein X represents at least one —CH$_2$CH(CH$_3$)—.

9. The compound as claimed in claim 1, wherein 80 to 100% of the X represents groups of the formula —CH$_2$CH$_2$—.

10. The compound as claimed in claim 1, wherein at least 25% of the Z are selected from the radicals of the formulae consisting of Z$^2$, Z$^3$, Z$^4$, Z$^5$ and Z$^6$.

11. The compound as claimed in claim 1, wherein at least 50% of the Z are selected from the radicals of the formulae consisting of Z$^2$, Z$^3$, Z$^4$, Z$^5$ and Z$^6$.

12. The compound as claimed in claim 1, wherein a compound consists of an ester based on malonic acid and diaminoethane that contains 4 propyleneoxide groups and 24 ethyleneoxide groups and oleic acid.

13. A compound having the structure of a modified block polymer (I), built up, corresponding to the formula, from a) 2 to 10 trivalent or tetravalent block oxyalkylate units based on diamines (aminoxyalkylates) having the general formula (Ia)

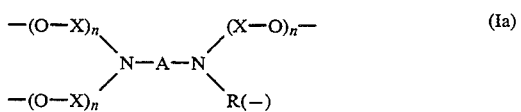

b) monovalent acid radicals symbolized by the general formula (Ib)

and c) divalent groups of the general formula (Ic)

where each of the free valences indicated in the formula units (Ia) is defined in a manner such that it is bonded, independently of one another, directly to one formula unit (Ib) in each case or to a valence of the formula unit (Ic), and where, in the formula units (Ia) to (Ic), A represents C$_2$-C$_{12}$-alkylene, C$_6$H$_{10}$-(C$_1$-C$_4$-alkylene)-C$_6$H$_{10}$, C$_6$-C$_{12}$-arylene, C$_7$-C$_{14}$-alkylarylene, C$_5$-C$_7$-cycloalkylene or C$_2$-C$_{24}$-alkylene, or represents a combination of the divalent groups listed and, X represents identical or different groups of the formulae —CH$_2$CH$_2$— or —CH$_2$CH—(CH$_3$)—, n represents identical or different numbers from 1 to 100, R represents a C$_1$-C$_3$-alkyl group or divalent group of the formula —(X—O)$_n$— with one free valence as defined above and indicated by (—), B represents a straight-chain C$_1$-C$_8$-alkylene, an alkylene radical of a dicarboxylic acid based on dimerized C$_{11}$-C$_{24}$-fatty acids, cyclohexylene, C$_5$-C$_{12}$-arylene or a group of the formula —CH=CH— or —CH$_2$CH(SO$_3$M)— in which M is a cation, Z represents identical or different radicals Z$^1$ to Z$^6$, in which Z$^1$ denotes hydrogen, Z$^2$ denotes an acyl radical of the formula R$^1$—CO— in which R$^1$ denotes a straight-chain, saturated or unsaturated C$_7$-C$_{21}$-aliphatic hydrocarbon radical which, in addition, is unsubstituted or substituted by one or two hydroxyl groups or by one C$_5$-C$_{12}$-aryl or C$_6$-C$_{12}$-hydroxyaryl radical, Z$^3$ denotes an acyl radical of the formula R$^2$—CO— in which R$^2$ denotes a straight-chain, branched or cyclic, saturated or unsaturated aliphatic hydrocarbon radical having 1 to 6 carbon atoms which, in addition, is unsubstituted or substituted by C$_6$-C$_{12}$-aryl, or denotes a phenyl or naphthyl radical or a monosubstituted to trisubstituted phenyl or naphthyl radical, the substituents being selected from the series consisting of C$_1$-C$_{12}$-alkyl, C$_1$-C$_{12}$-alkoxy, sulfo, hydroxyl, amino, C$_1$-C$_{12}$alkylamino, di-(C$_1$-C$_{12}$-alkyl)amino, C$_2$-C$_5$-acylamido, acetoacetamido, aminocarbonyl, C$_1$-C$_4$-alkylaminocarbonyl and di-(C$_1$-C$_4$-alkyl)aminocarbonyl, Z$^4$ denotes an acyl radical of a monofunctional resin acid of the colophonium type, Z$^5$ denotes an acyl radical of the formula —CO—B—COOM in which B has the defined meaning and M represents a cation, and Z$^6$ denotes an acyl radical of the formula —CO—B—COO—(X—O)$_m$—Y—R$^3$, in which B and X have the meanings mentioned, Y is a direct bond or a group of the formula CO, m is a number from 1 to 150 in the case where Y=CO and a number from 0 to 150 in the case where Y=a direct bond, and R$^3$ is a saturated or unsaturated aliphatic, aromatic or araliphatic C$_3$-C$_{24}$-hydrocarbon radical where at least one radical Z represents a radical from the group consisting of Z$^2$, Z$^4$ and Z$^6$.

14. The compound as claimed in claim 13, wherein Z represents a radical selected from the group consisting of Z$^4$ and Z$^6$.

15. The compound as claimed in claim 13, wherein Z represents a combination of Z$^2$ with one or more radicals Z$^3$, Z$^4$, or Z$^6$.

16. The compound as claimed in claim 13, wherein 80 to 100% of the X represents groups of the formula —CH$_2$CH$_2$—.

17. The compound as claimed in claim 13, wherein at least 25% of the Z are selected from the radicals of the formulae consisting of Z$^2$, Z$^3$, Z$^4$, Z$^5$ and Z$^6$.

18. The compound as claimed in claim 13, wherein at least 50% of the Z are selected from the radicals of the formulae consisting of Z$^2$, Z$^3$, Z$^4$, Z$^5$ and Z$^6$.

19. A compound having the structure of a modified block polymer (I), built up, corresponding to the formula, from a) 1 to 10 trivalent or tetravalent block oxyalkylate units based on diamines (aminoxyalkylates) having the general formula (Ia)

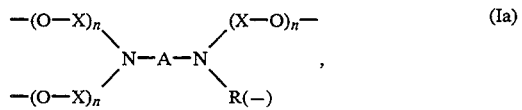

b) monovalent acid radicals symbolized by the general formula (Ib)

$$-Z \qquad \text{(Ib)},$$

and, when two or more formula units (Ia) are present, additionally from c) divalent groups of the general formula (Ic)

$$-CO-B-CO- \qquad \text{(Ic)},$$

where each of the free valences indicated in the formula units (Ia) is defined in a manner such that it is bonded, independently of one another, directly to one formula unit (Ib) in each case or to a valence of the formula unit (Ic), and where, in the formula units (Ia) to (Ic), A represents C$_2$-C$_{12}$-alkylene, C$_6$H$_{10}$-(C$_1$-C$_4$-alkylene)—C$_6$H$_{10}$, C$_6$-C$_{12}$-arylene, C$_7$-C$_{14}$-alkylarylene, C$_5$-C$_7$-cycloalkylene, C$_2$-C$_{24}$-alkylene or represents a combination of the divalent groups listed and, X represents identical or different groups of the formulae —CH$_2$CH$_2$— or —CH$_2$CH(CH$_3$)—, n represents identical or different numbers from 1 to 100, R represents a C$_1$-C$_3$-alkyl group or divalent group of the formula —(X—0)$_n$— with one free valence as defined above and indicated by (—), B represents a straight-chain C$_1$-C$_8$-alkylene, an alkylene radical of a dicarboxylic acid based on dimerized C$_{11}$-C$_{24}$-fatty acids, cyclohexylene, C$_5$-C$_{12}$-arylene or a group of the formula —CH=CH— or —CH$_2$CH(SO$_3$M)— in which M is a cation, Z represents identical or different radicals Z$^1$ to Z$^6$, in which Z$^1$ denotes hydrogen, Z$^2$ denotes an acyl radical of the formula R$^1$—CO— in which R$^1$ denotes a straight-chain, saturated or unsaturated C$_7$-C$_{21}$-aliphatic hydrocarbon radical which, in addition, is unsubstituted or substituted by one or two hydroxyl groups or by one C$_5$-C$_2$-aryl or C$_6$-C$_{12}$-hydroxyaryl radical, Z$^3$ denotes an acyl radical of the formula R$^2$—CO— in which R$^2$ denotes a straight-chain, branched or cyclic, saturated or unsaturated aliphatic hydrocarbon radical having 1 to 6 carbon atoms which, in addition, is unsubstituted or substituted by C$_6$-C$_{12}$-aryl, or denotes a phenyl or naphthyl radical or a monosubstituted to trisubstituted phenyl or naphthyl radical, the substituents being selected from the series consisting of C$_1$-C$_{12}$-alkyl, C$_1$-C$_{12}$-alkoxy, sulfo, hydroxyl, amino, C$_1$-C$_{12}$-alkylamino, di-(C$_1$-C$_{12}$-alkyl)amino, C$_2$-C$_5$-acylamido, aceto-acetamido, aminocarbonyl, C$_1$-C$_4$-alkylaminocarbonyl and di-(C$_1$-C$_4$-alkyl)aminocarbonyl, Z$^4$ denotes an acyl radical of a monofunctional resin acid of the colophonium type, $Z^5$ denotes an acyl radical of the formula —CO—B—COOM in which B has the defined meaning and M represents a cation, and $Z^6$ denotes an acyl radical of the formula —CO—B—COO—(X—O)$_m$—Y—R$^3$, in which B and X have the meanings mentioned, Y is a direct bond or a group of the formula CO, m is a number from 1 to 150 in the case where Y=CO and a number from 0 to 150 in the case where Y=a direct bond, and R$^3$ is a saturated or unsaturated aliphatic, aromatic or araliphatic $C_3$-$C_{24}$-hydrocarbon radical;

wherein at least one Z represents a radical selected from the group consisting of $Z^4$ and $Z^6$.

20. A compound having the structure of a modified block polymer (I), built up, corresponding to the formula, from a) 1 to 10 trivalent or tetravalent block oxyalkylate units based on diamines (aminoxyalkylates) having the general formula (Ia)

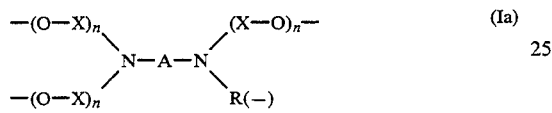

b) monovalent acid radicals symbolized by the general formula (Ib)

—Z     (Ib), and, when two or more formula units (Ia) are present, additionally from c) divalent groups of the general formula (Ic)

—CO—B—CO—     (Ic), where each of the free valences indicated in the formula units (Ia) is defined in a manner such that it is bonded, independently of one another, directly to one formula unit (Ib) in each case or to a valence of the formula unit (Ic), and where, in the formula units (Ia) to (Ic), A represents $C_2$-$C_{12}$-alkylene, $C_6H_{10}$-($C_1$-$C_4$-alkylene)-$C_6H_{10}$, $C_6$-$C_{12}$-arylene, $C_7$-$C_{14}$-alkylarylene, $C_5$-$C_7$-cycloalkylene, $C_2$-$C_{24}$-alkylene or represents a combination of the divalent groups listed and, X represents identical or different groups of the formulae —CH$_2$CH$_2$— or —CH$_2$CH(CH$_3$)—, n represents identical or different numbers from 1 to 100, R represents a $C_1$-$C_3$-alkyl group or divalent group of the formula —(X—O)$_n$— with one free valence as defined above and indicated by (—), B represents a straight-chain $C_1$-$C_8$-alkylene, an alkylene radical of a dicarboxylic acid based on dimerized $C_{11}$-$C_{24}$-fatty acids, cyclohexylene, $C_5$-$C_{12}$-arylene or a group of the formula —CH=CH— or —CH$_2$CH(SO$_3$M)— in which M is a cation, Z represents identical or different radicals $Z^1$ to $Z^6$, in which $Z^1$ denotes hydrogen, $Z^2$ denotes an acyl radical of the formula R$^1$—CO— in which R$^1$ denotes a straight-chain, saturated or unsaturated $C_7$-$C_{21}$-aliphatic hydrocarbon radical which, in addition, is unsubstituted or substituted by one or two hydroxyl groups or by one $C_5$-$C_{12}$-aryl or $C_6$-$C_{12}$-hydroxyaryl radical, $Z^3$ denotes an acyl radical of the formula R$^2$—CO— in which R$^2$ denotes a straight-chain, branched or cyclic, saturated or unsaturated aliphatic hydrocarbon radical having 1 to 6 carbon atoms which, in addition, is unsubstituted or substituted by $C_6$-$C_{12}$-aryl, or denotes a phenyl or naphthyl radical or a monosubstituted to trisubstituted phenyl or naphthyl radical, the substituents being selected from the series consisting of $C_1$-$C_{12}$-alkyl, $C_1$-$C_{12}$-alkoxy, sulfo, hydroxyl, amino, $C_1$-$C_{12}$-alkylamino, di-($C_1$-$C_{12}$-alkyl)amino, $C_2$-$C_5$-acylamido, aceto-acetamido, aminocarbonyl, $C_1$-$C_4$-alkylaminocarbonyl and di-($C_1$-$C_4$-alkyl)aminocarbonyl, $Z^4$ denotes an acyl radical of a monofunctional resin acid of the colophonium type, $Z^5$ denotes an acyl radical of the formula —CO—B—COOM in which B has the defined meaning and M represents a cation, and $Z^6$ denotes an acyl radical of the formula —CO—B—COO—(X—O)$_m$—Y—R$^3$, in which B and X have the meanings mentioned, Y is a direct bond or a group of the formula CO, m is a number from 1 to 150 in the case where Y=CO and a number from 0 to 150 in the case where Y=a direct bond, and R$^3$ is a saturated or unsaturated aliphatic, aromatic or araliphatic $C_3$-$C_{24}$-hydrocarbon radical;

wherein Z represents a combination of $Z^2$ with at least two different radicals selected from the group consisting of $Z^3$, $Z^4$, $Z^5$ and $Z^6$.

* * * * *